(12) United States Patent
Graham et al.

(10) Patent No.: US 10,132,714 B2
(45) Date of Patent: Nov. 20, 2018

(54) DETECTION APPARATUS AND METHOD

(71) Applicant: Wellstream International Limited, Newcastle-Upon-Tyne (GB)

(72) Inventors: Geoffrey Stephen Graham, Newcastle-Upon-Tyne (GB); Phillip Edward Harley, Newcastle-Upon-Tyne (GB); William James Shephard, Newcastle-Upon-Tyne (GB)

(73) Assignee: GE Oil & Gas UK Limited, Bristol (GB)

(*) Notice: Subject to any disclaimer, the term of this patent is extended or adjusted under 35 U.S.C. 154(b) by 581 days.

(21) Appl. No.: 13/963,207

(22) Filed: Aug. 9, 2013

(65) Prior Publication Data

US 2014/0069542 A1    Mar. 13, 2014

(30) Foreign Application Priority Data

Sep. 10, 2012  (EP) .................................... 12183754

(51) Int. Cl.
| | |
|---|---|
| *G01M 3/40* | (2006.01) |
| *G01N 17/02* | (2006.01) |
| *F16L 55/07* | (2006.01) |
| *G01M 3/18* | (2006.01) |

(52) U.S. Cl.
CPC .............. *G01M 3/40* (2013.01); *F16L 55/07* (2013.01); *G01M 3/18* (2013.01); *G01N 17/02* (2013.01); *Y10T 29/49826* (2015.01)

(58) Field of Classification Search
CPC .......... G01M 3/40; G01M 3/18; G01N 17/02; F16L 55/07
USPC ........................................................ 324/637
See application file for complete search history.

(56) References Cited

U.S. PATENT DOCUMENTS

| | | |
|---|---|---|
| 3,600,674 A | 8/1971 | Roberts |
| 4,099,117 A | 7/1978 | Erath |
| 4,322,805 A | 3/1982 | Rog et al. |
| 4,695,787 A * | 9/1987 | Billet ...................... G01V 1/201 |
| | | 324/557 |

(Continued)

FOREIGN PATENT DOCUMENTS

| | | |
|---|---|---|
| CN | 1030299 A | 1/1989 |
| CN | 2090533 U | 12/1991 |

(Continued)

OTHER PUBLICATIONS

European Search Report dated Jul. 15, 2013, for corresponding EP Divisional Application No. 1316142.2 which corresponds to EP 12183754.6 to which U.S. Appl. No. 13/963,207 claims priority.

(Continued)

*Primary Examiner* — Son Le
*Assistant Examiner* — Akm Zakaria
(74) *Attorney, Agent, or Firm* — Reza Mollaaghababa; Thomas J. Engellenner; Pepper Hamilton LLP

(57) ABSTRACT

A first embodiment of a detection apparatus arranged to detect defects within a flexible pipe body comprises a signal generator, a receiver, a correlator and a processor. A second embodiment of a detection apparatus arranged to detect defects within a flexible pipe at least partially surrounded by seawater comprises an impedance monitor and a processor. Methods of detecting defects within a flexible pipe body, a pipeline apparatus and methods of forming pipeline apparatuses are also disclosed.

11 Claims, 9 Drawing Sheets

(56) References Cited

U.S. PATENT DOCUMENTS

| | | | |
|---|---|---|---|
| 5,126,654 A * | 6/1992 | Murphy | G01N 17/02 204/196.06 |
| 5,485,100 A * | 1/1996 | Kogut | G01R 17/06 324/610 |
| 6,008,658 A | 12/1999 | Suyama et al. | |
| 6,509,557 B1 * | 1/2003 | Bass | H05B 6/108 219/772 |
| 7,924,032 B1 * | 4/2011 | Miller | G01N 17/02 324/527 |
| 9,400,227 B2 * | 7/2016 | Ramos | G01M 3/002 |
| 2008/0246667 A1 * | 10/2008 | Symons | G06K 19/0723 343/702 |
| 2009/0223284 A1 | 9/2009 | Buhring | |
| 2010/0001741 A1 * | 1/2010 | Bier | G01M 3/18 324/600 |
| 2011/0155933 A1 | 6/2011 | Buhring | |
| 2013/0218485 A1 * | 8/2013 | Hansen | G01M 5/0025 702/38 |

FOREIGN PATENT DOCUMENTS

| | | |
|---|---|---|
| CN | 2249412 Y | 3/1997 |
| CN | 1183142 A | 5/1998 |
| CN | 1625682 A | 6/2005 |
| CN | 2708312 Y | 7/2005 |
| CN | 101046466 A | 10/2007 |
| CN | 101283258 A | 10/2008 |
| CN | 102269642 A | 12/2011 |
| DE | 19805263 | 8/1999 |
| EP | 0298479 | 1/1989 |
| JP | 57114832 A | 7/1982 |
| WO | 2008083409 | 7/2008 |

OTHER PUBLICATIONS

Office Action and Search Report for corresponding Chinese Application 201310389155.4, dated Dec. 19, 2016; 15 pages.

* cited by examiner

DETECTION APPARATUS AND METHOD

FIELD OF THE INVENTION

The present invention relates to a detection apparatus and method. In particular, the present invention relates to a detection apparatus arranged to detect defects within a flexible pipe body, and a method of detecting defects or changes of condition of a pipe body. Particular embodiments relate to a flexible pipe comprising a flexible pipe body and the detection apparatus, a method of forming such a flexible pipe, and a method of operating such a flexible pipe. Certain embodiments of the present invention are also arranged to detect a change in condition of a pipe body.

BACKGROUND OF THE INVENTION

Traditionally flexible pipe is utilised to transport production fluids, such as oil and/or gas and/or water, from one location to another. Flexible pipe is particularly useful in connecting a sub-sea location (which may be deep underwater, say 1000 metres or more) to a sea level location. The pipe may have an internal diameter of typically up to around 0.6 metres. Flexible pipe is generally formed as an assembly of a flexible pipe body and one or more end fittings. The pipe body is typically formed as a combination of layered materials that form a pressure-containing conduit. The pipe structure allows large deflections without causing bending stresses that impair the pipe's functionality over its lifetime. The pipe body is generally built up as a combined structure including metallic and polymer layers.

In many known flexible pipe designs the pipe body includes one or more pressure armour layers. The primary load on such layers is formed from radial forces. Pressure armour layers often have a specific cross section profile to interlock so as to be able to maintain and absorb radial forces resulting from outer or inner pressure on the pipe. The cross sectional profile of the wound wires which thus prevent the pipe from collapsing or bursting as a result of pressure are sometimes called pressure-resistant profiles. When pressure armour layers are formed from helically wound wired forming hoop components, the radial forces from outer or inner pressure on the pipe cause the hoop components to expand or contract, putting a tensile load on the wires.

In many known flexible pipe designs the pipe body includes one or more tensile armour layers. The primary loading on such a tensile armour layer is tension. In high pressure applications, such as in deep and ultra deep water environments, the tensile armour layer experiences high tension loads from a combination of the internal pressure end cap load and the self-supported weight of the flexible pipe. This can cause failure in the flexible pipe since such conditions are experienced over prolonged periods of time.

Unbonded flexible pipe has been used for deep water (less than 3,300 feet (1,005.84 metres)) and ultra deep water (greater than 3,300 feet) developments. It is the increasing demand for oil which is causing exploration to occur at greater and greater depths where environmental factors are more extreme. For example, in such deep and ultra-deep water environments, ocean floor temperature increases the risk of production fluids cooling to a temperature that may lead to pipe blockage. Increased depths also increase the pressure associated with the environment in which the flexible pipe must operate. As a result the need for high levels of performance from the layers of the flexible pipe body is increased. Flexible pipe may also be used for shallow water applications (for example less than around 500 metres depth) or even for shore (overland) applications.

One way to improve the load response and thus performance of armour layers is to manufacture the layers from thicker and stronger and thus more robust materials. For example, for pressure armour layers in which the layers are often formed from wound wires with adjacent windings in the layer interlocking, manufacturing the wires from thicker material results in the strength increasing appropriately. However, as more material is used, the weight of the flexible pipe increases. Ultimately the weight of the flexible pipe can become a limiting factor in using flexible pipe. Additionally manufacturing flexible pipe using thicker and thicker material increases material costs appreciably, which is also a disadvantage.

Regardless of measures taken to improve the performance of armour layers within a pipe body, there remains a risk of defects arising within a flexible pipe. A defect may comprise damage to an outer wall of a flexible pipe body resulting in the ingress of seawater into an annulus within the pipe body such that seawater fills voids between the armour layer wires and other structural elements of the pipe. Armour layer wires and other structural elements are typically manufactured from steel or other metallic materials, which are vulnerable to accelerated corrosion upon contact with seawater. If such a defect is not detected promptly then the structural integrity of the pipe body can be compromised. Detection of defects has previously often required visual inspection of the pipe body, which can be hazardous, particularly for deep water and ultra-deep water installations. Furthermore, certain changes in condition of a flexible pipe, including bending, crushing and large temperature variations can lead to defects, if left unchecked. Such changes in condition have previously often only been detectable through visual inspection.

SUMMARY OF THE INVENTION

Certain embodiments of the invention provide the advantage that a defect within a pipe body can be detected without requiring periodic visual inspection. Defects can then be repaired, or the pipe body replaced. Detectable defects include a breach of the outer wall of a flexible pipe and the ingress of seawater into a pipe body annulus. Certain embodiments can also provide an indication of changes in the condition of the pipe body, for instance due to crushing or bending applied to the pipe body, or variation in temperature along the length of the pipe body.

According to a first aspect of the present invention there is provided a detection apparatus arranged to detect defects within a flexible pipe, the detection apparatus comprising: a signal generator arranged to couple to first and second electrically conductive members extending at least partially along the length of a flexible pipe and electrically isolated from one another to form an electrical transmission line, the signal generator being arranged to generate an electrical test signal and to apply the test signal between the first and second electrically conductive members, the test signal comprising a pulse code modulated electrical signal; a receiver arranged to couple to the first and second electrically conductive members and to receive an electrical return signal comprising a reflection of the test signal; a correlator arranged to correlate the test signal with the return signal and to determine a correlation signal; and a processor arranged to detect variation of the correlation signal, and to determine if a detected variation is indicative of a pipe defect.

The pipe may be for high pressure use in oil and gas extraction.

The signal generator may be arranged to generate a test signal comprising a random or pseudo-random series of pulses. In particular, the signal generator may be arranged to generate a test signal comprising a continuous pulse code modulated electrical signal or bursts of a pulse code modulated electrical signal.

The processor may be arranged to detect a feature in the correlation signal and to determine a corresponding spatial position along the flexible pipe body from the correlation delay corresponding to the feature from the predetermined propagation speed of the electrical transmission line. The processor may be further arranged to determine the magnitude of the feature in the correlation signal and, to determine a corresponding magnitude of a local variation in the characteristics of the electrical transmission line. The processor may be further arranged to determine the nature of the physical event associated with the feature.

The processor may be arranged to generate an output signal indicating that a correlation signal variation indicative of a pipe body defect or a change in condition of the pipe body has been detected. The processor may be further arranged to generate an output signal indicating a corresponding spatial position along the flexible pipe body for a local variation in the characteristic impedance of the electrical transmission line.

According to a second aspect of the present invention there is provided a method of detecting defects within a flexible pipe, the method comprising: coupling a signal generator to first and second electrically conductive members extending at least partially along the length of a flexible pipe and electrically isolated from one another to form an electrical transmission line; generating at the signal generator an electrical test signal comprising a pulse code modulated electrical signal; applying the test signal between the first and second electrically conductive members; coupling a receiver to the first and second electrically conductive members; receiving an electrical return signal comprising a reflection of the test signal; correlating the test signal with the return signal to determine a correlation signal; detecting variation of the correlation signal; and determining if a detected variation is indicative of a pipe defect.

According to a third aspect of the present invention there is provided a pipeline apparatus comprising: a pipe body including first and second electrically conductive members extending at least partially along the length of the pipe body and electrically isolated from one another to form an electrical transmission line; an end fitting coupled to at least one end of the pipe body; and a detection apparatus according to the first aspect of the present invention coupled to an end fitting coupled to an end of the flexible pipe body, wherein the signal generator is coupled to the first and second electrically conductive members.

At least one electrically conductive member may comprise a metallic structural member of the pipe body, electrically isolated within the pipe body structure. At least one electrically conductive member may comprise a suitably conductive tape element (for instance a metallic wire or cable) extending through the pipe body between an innermost barrier layer and an outermost barrier layer. One member may comprise the structure of the pipe, for instance a layer or armour wire and the other member may comprise a structural element which is electrically isolated from the surrounding structural elements.

The pipeline apparatus may further comprise a second detection apparatus, the second detection apparatus comprising: an impedance monitor coupled to and arranged to measure the impedance between an electrically conductive member extending at least partially along the length of the pipe body and a seawater electrode in contact with seawater surrounding at least part of the pipe body in response to an electrical test signal applied to the electrically conductive member at first and second frequencies; and a processor arranged to detect variation of the measured impedance for an electrical test signal at a first frequency, and if a variation of the measured impedance is detected, to determine if the variation is indicative of a pipe defect, and if so to determine the distance from the seawater electrode to a pipe defect by comparison of the measured impedances at the first and second frequencies.

The first and second electrically conductive members forming the transmission line may comprise first and second metallic structural members of the pipe body and the electrically conductive member coupled to the impedance monitor comprises one of the first and second metallic structural members.

According to a fourth aspect of the present invention there is provided a method of forming a pipeline apparatus, the method comprising: providing a pipe body including first and second electrically conductive members extending at least partially along the length of the pipe body and electrically isolated from one another to form an electrical transmission line; and coupling an end fitting to at least one end of the pipe body; wherein a detection apparatus according to the first aspect of the present invention is coupled to an end fitting coupled to an end of the pipe body, the method further comprising coupling the signal generator to the first and second electrically conductive members.

According to a fifth aspect of the present invention there is provided a detection apparatus arranged to detect defects within a flexible pipe at least partially surrounded by seawater, the detection apparatus comprising: an impedance monitor arranged to measure the impedance between an electrically conductive member extending at least partially along the length of a flexible pipe and a separate seawater electrode in contact with seawater surrounding at least part of the flexible pipe in response to an electrical test signal applied to the electrically conductive member at first and second frequencies; and a processor arranged to detect variation of the measured impedance for an electrical test signal at a first frequency, and if a variation of the measured impedance is detected, to determine if the variation is indicative of a pipe defect, and if so to determine the distance from the seawater electrode to a pipe defect by comparison of the measured impedances at the first and second frequencies.

The pipe may have an outer electrically isolating layer such that before any defect occurs there is no electrical conduction between the electrically conductive member and seawater.

The impedance monitor may be arranged to apply electrical test signals to the electrically conductive member at a plurality of frequencies between 10 Hz and 100 kHz.

The impedance monitor may comprise a current source arranged to supply an electrical test signal to the electrically conductive member, and a voltage meter arranged to determine the generated voltage at the electrically conductive member relative to the seawater electrode.

The voltage meter may be a synchronous demodulator and the impedance monitor may further comprise a controller arranged to provide a frequency control signal to the current source and the synchronous demodulator to ensure that the voltage measurements are synchronised to the current source.

According to a sixth aspect of the present invention there is provided a method of detecting defects within a flexible pipe at least partially surrounded by seawater, the method comprising: coupling an impedance monitor between an electrically conductive member extending at least partially along the length of a flexible pipe and a seawater electrode in contact with seawater surrounding at least part of the flexible pipe; generating an electrical test signal at the impedance monitor and applying the test signal to the electrically conductive member at first and second frequencies; detecting variation of the measured impedance for an electrical test signal at a first frequency; and determining if a detected impedance variation is indicative of a pipe defect, and if so determining a distance from the seawater electrode to a pipe defect by comparison of the measured impedances at the first and second frequencies.

According to a seventh aspect of the present invention there is provided a pipeline apparatus comprising: a pipe body including an electrically conductive member extending at least partially along the length of the pipe body; an end fitting coupled to at least one end of the pipe body; a seawater electrode; and a detection apparatus according to the fifth aspect of the present invention coupled to an end fitting coupled to an end of the pipe body, wherein the impedance monitor is coupled to the electrically conductive member and the seawater electrode.

The electrically conductive member may comprise a metallic structural member of the pipe body. Alternatively, the electrically conductive member may comprise another suitably conductive tape element (for instance a metallic wire or cable) extending through the pipe body between an innermost barrier layer and an outermost barrier layer.

The pipeline apparatus may further comprise a second detection apparatus, the second detection apparatus comprising: a signal generator coupled to a pair of electrically conductive members extending at least partially along the length of the pipe body and electrically isolated from one another to form an electrical transmission line, the signal generator being arranged to generate an electrical test signal and to apply the test signal between the pair of electrically conductive members, the test signal comprising a pulse code modulated electrical signal; a receiver coupled to the pair of electrically conductive members and arranged to receive an electrical return signal comprising a reflection of the test signal; a correlator arranged to correlate the test signal with the return signal and to determine a correlation signal; and a processor arranged to detect variation of the correlation signal, and to determine if a detected variation is indicative of a pipe defect.

The pair of electrically conductive members may comprise the first metallic structural member of the pipe body and a second metallic structural member of the pipe body.

According to an eighth aspect of the present invention there is provided a method of forming a pipeline apparatus, the method comprising: providing a pipe body including an electrically conductive member extending at least partially along the length of the pipe body; providing a seawater electrode; and coupling an end fitting to at least one end of the pipe body; wherein a detection apparatus according to the fifth aspect of the present invention is coupled to an end fitting coupled to an end of the pipe body, the method further comprising coupling the impedance monitor to the electrically conductive member and the seawater electrode.

BRIEF DESCRIPTION OF THE DRAWINGS

Embodiments of the invention are further described hereinafter with reference to the accompanying drawings, in which.

In the drawings like reference numerals refer to like parts.

DETAILED DESCRIPTION OF THE INVENTION

Figure 1:
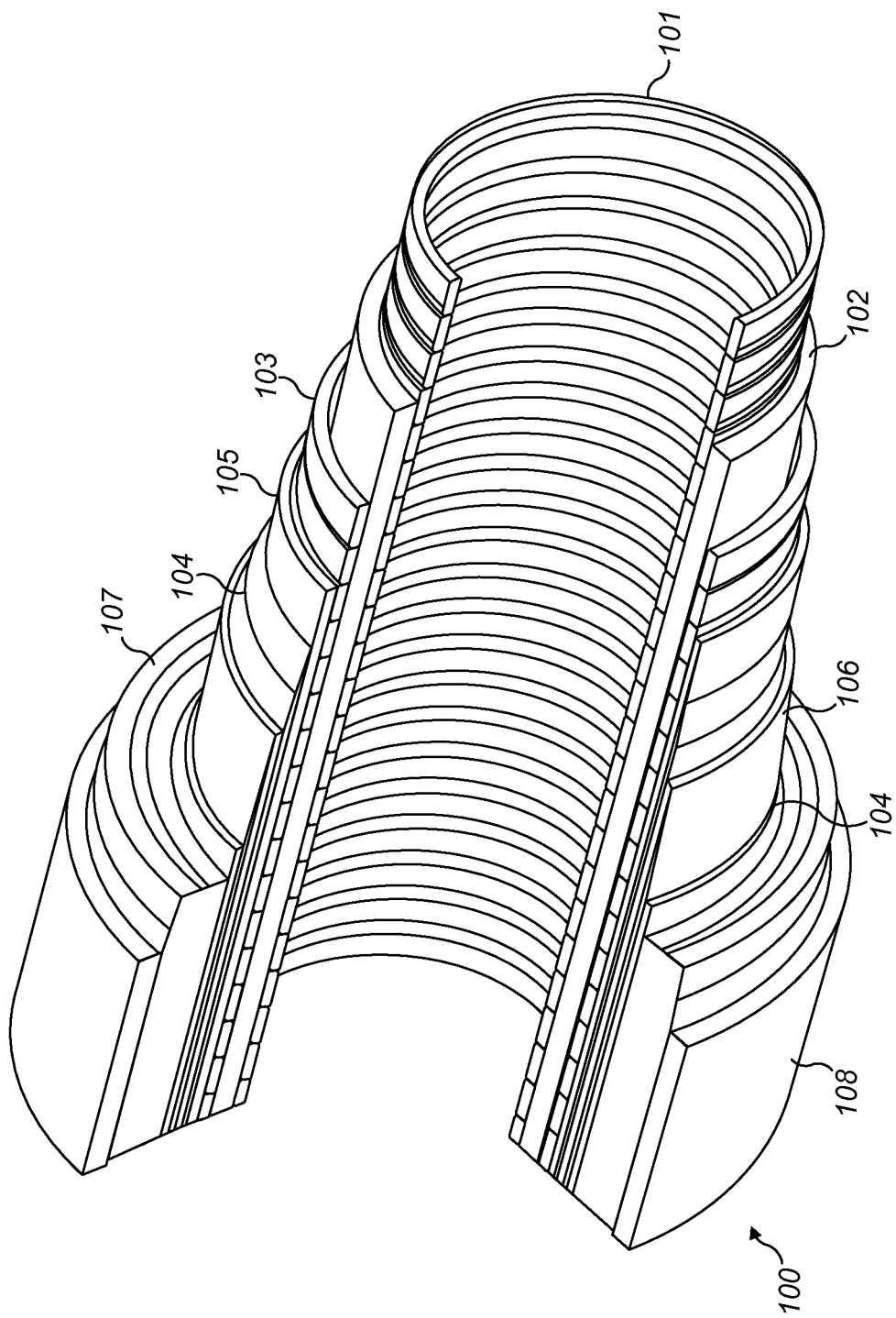
FIG. 1 illustrates a flexible pipe body.

Throughout this description, reference will be made to a flexible pipe. It will be understood that a flexible pipe is an assembly of a portion of a pipe body and one or more end fittings in each of which a respective end of the pipe body is terminated. FIG. 1 illustrates how pipe body 100 is formed in accordance with an embodiment of the present invention from a combination of layered materials that form a pressure-containing conduit. Although a number of particular layers are illustrated in FIG. 1, it is to be understood that the present invention is broadly applicable to coaxial pipe body structures including two or more layers manufactured from a variety of possible materials. It is to be further noted that the layer thicknesses are shown for illustrative purposes only.

As illustrated in FIG. 1, a pipe body includes an optional innermost carcass layer 101. The carcass provides an interlocked construction that can be used as the innermost layer to prevent, totally or partially, collapse of an internal pressure sheath 102 due to pipe decompression, external pressure, and tensile armour pressure and mechanical crushing loads. It will be appreciated that certain embodiments of the present invention are applicable to 'smooth bore' operations (i.e. without a carcass) as well as such 'rough bore' applications (with a carcass).

The internal pressure sheath 102 acts as a fluid retaining layer and comprises a polymer layer that ensures internal fluid integrity. It is to be understood that this layer may itself comprise a number of sub-layers. It will be appreciated that when the optional carcass layer is utilised the internal pressure sheath is often referred to by those skilled in the art as a barrier layer. In operation without such a carcass (so-called smooth bore operation) the internal pressure sheath may be referred to as a liner.

An optional pressure armour layer 103 is a structural layer with a lay angle close to 90° that increases the resistance of the flexible pipe to internal and external pressure and mechanical crushing loads. The layer also structurally supports the internal pressure sheath, and typically consists of an interlocked construction.

The flexible pipe body also includes an optional first tensile armour layer 105 and optional second tensile armour layer 106. Each tensile armour layer is a structural layer with a lay angle typically between 10° and 55°. Each layer is used to sustain tensile loads and internal pressure. The tensile armour layers are often counter-wound in pairs.

The flexible pipe body shown also includes optional layers of tape 104 which help contain underlying layers and to some extent prevent abrasion between adjacent layers.

The flexible pipe body also typically includes optional layers of insulation 107 and an outer sheath 108, which comprises a polymer layer used to protect the pipe against penetration of seawater and other external environments, corrosion, abrasion and mechanical damage.

Each flexible pipe comprises at least one portion, sometimes referred to as a segment or section of pipe body 100 together with an end fitting located at one end or both ends of the flexible pipe. An end fitting provides a mechanical device which forms the transition between the flexible pipe body and a connector. The different pipe layers as shown, for example, in FIG. 1 are terminated in the end fitting in such a way as to transfer the load between the flexible pipe and the connector.

Figure 2:
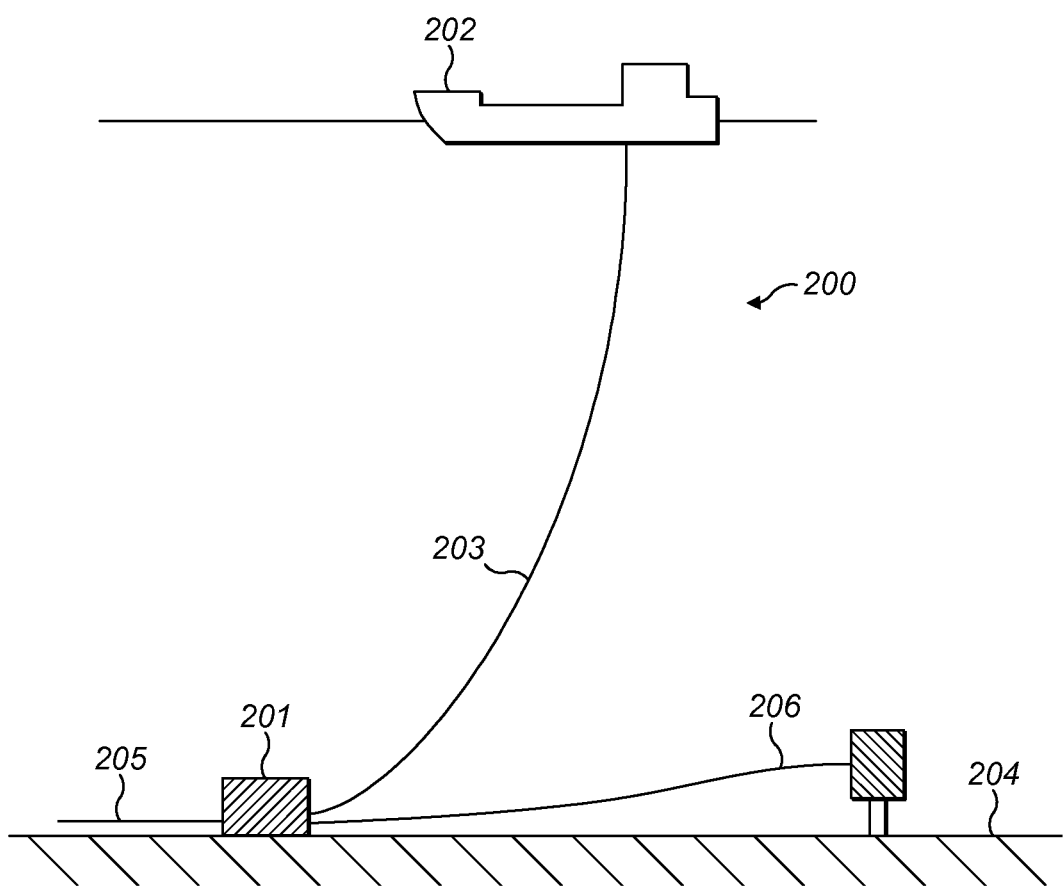
FIG. 2 illustrates a riser assembly incorporating a flexible pipe body.

FIG. 2 illustrates a riser assembly 200 suitable for transporting production fluid such as oil and/or gas and/or water from a sub-sea location 201 to a floating facility 202. For example, in FIG. 2 the sub-sea location 201 includes a sub-sea flow line 205. The flexible flow line 205 comprises a flexible pipe, wholly or in part, resting on the sea floor 204 or buried below the sea floor and used in a static application. The floating facility may be provided by a platform and/or buoy or, as illustrated in FIG. 2, a ship. The riser assembly 200 is provided as a flexible riser, that is to say a flexible pipe 203 connecting the ship to the sea floor installation. The flexible pipe may be in segments of flexible pipe body with connecting end fittings. FIG. 2 also illustrates how portions of flexible pipe can be utilised as a flow line 205 or jumper 206. It will be appreciated that there are different types of riser, as is well-known by those skilled in the art. Embodiments of the present invention may be used with any type of riser, such as a freely suspended (free, catenary riser), a riser restrained to some extent (buoys, chains), totally restrained riser or enclosed in a tube (I or J tubes).

As noted above, defects in a flexible pipe body can compromise the structural integrity of the pipe body. In particular, a breach or rupture of an outer seawater resistant layer can allow seawater ingress into the pipe body annulus between an innermost barrier layer and the outer seawater resistant layer. With reference to FIG. 1 the outer seawater resistant layer may comprise the polymer outer sheath 108 and the innermost barrier layer may comprise the internal pressure sheath 102. The pipe body annulus is occupied by metallic structural components such as the tensile armour layers 105, 106 of FIG. 1. Such components are frequently formed from steel or other metals and are susceptible to rapid corrosion in the presence of seawater. There will now be described embodiments of the present invention which can detect a breach of an outer resistant layer of a flexible pipe body. Certain embodiments can also detect other variations in the condition of a flexible pipe body, including crushing, bending and temperature variation.

Figure 3:
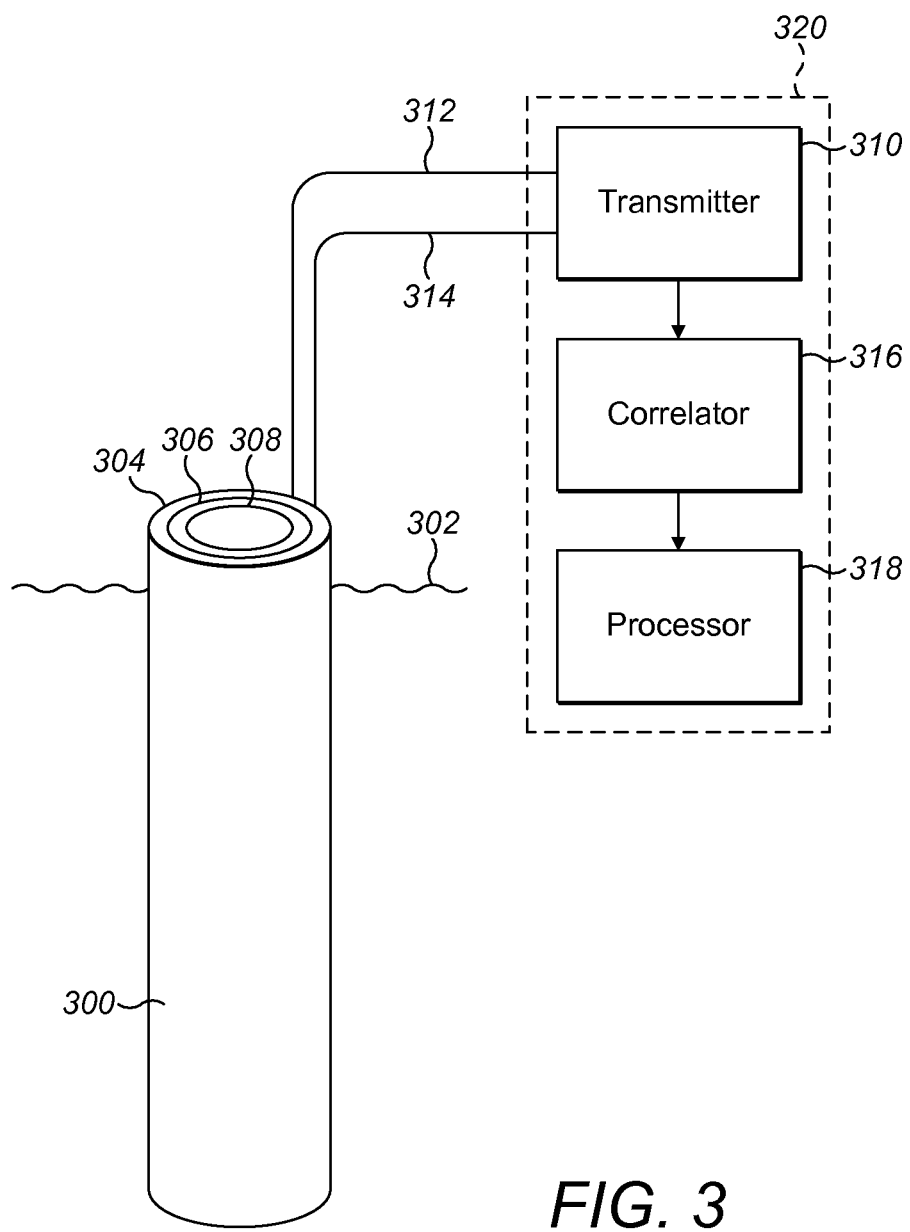
FIG. 3 illustrates a detection apparatus in accordance with a first embodiment of the invention.

FIG. 3 illustrates a detection apparatus in accordance with a first embodiment of the present invention coupled to a flexible pipe body. The detection apparatus is arranged to detect a change to a flexible pipe body which may indicate either a defect (and in particular a breach allowing seawater or other fluids into the pipe body annulus) or certain forms of change of condition as discussed above. The detection apparatus may be coupled to a warning system arranged to provide an output signal to an operator of the flexible pipe alerting the operator to potential damage to the pipe. The output signal may, for instance, be a visual or audible alarm.

FIG. 3 shows a flexible pipe 300, which as discussed above may form a riser. The pipe is at least partially surrounded by seawater, schematically illustrated by the pipe extending below the surface level 302 of the sea. As discussed above, a flexible pipe body is constructed from multiple layers of polymer barrier, including an outer seawater resistant layer 304 and at least first and second layers of co-axial metallic structural elements indicated 306, 308. The metallic structural elements, for instance the tensile armour layers 105, 106 of FIG. 1, are designed to satisfy purely mechanical properties of the structure of the pipe body. However, provided at least two of the metallic components, for instance individual tensile armour wires or separate armour wire layers as shown in FIG. 3, are electrically isolated from each other by an insulating medium, for instance the tape layers 104 of FIG. 1, then it can be considered that those components comprise first and second electrically conductive members 306, 308 extending at least partially along the length of a flexible pipe body. It will be appreciated by the appropriately skilled person that the electrically conductive members 306, 308 form an electrical transmission line capable of transmitting electrical signals. In particular, if the selected metallic components comprise first and second layers within the pipe body structure then the electrically conductive members 306, 308 form a coaxial electrical transmission line.

The skilled person will appreciate that a pair of electrically conductive members 306, 308 which are insulated from one another and extending at least partially along the length of a flexible pipe will transmit high frequency electrical signals which are applied at a first end of the pipe, as is the case for any electrical transmission line. The electrical signals are supplied by a signal generator electrically coupled to both members such that the electrical signal is applied between the members 306, 308. At high frequencies transmission lines possess resonant properties associated with their length, diameter, construction, and the dielectric properties of an insulator between the conductive members, which may be characterised by impedance and signal propagation speed (usually expressed as a fraction of the speed of light, c).

A notable characteristic of electrical transmission lines is that unless the end is correctly terminated with a matching impedance, electrical energy is reflected back along the line towards the source. For a flexible pipe, typically the electrically conductive members 306, 308 are not electrically coupled at either end of the flexible pipe. Even if electrical coupling is provided at a subsea end of the pipe, it is unlikely that the electrical coupling would have an impedance matched to the characteristic impedance of the transmission line. The reflected electrical energy can be received at a receiver. The skilled person will appreciate that the signal generator and the receiver may be combined, in the form of a transceiver. Electrical energy is also reflected by variations in the characteristic impedance along the length of the line. Specifically, partial reflections of the supplied electrical test signal are generated whenever there is a change in the characteristic impedance along the length of a transmission line. For the example of a flexible pipe body, if seawater enters the annulus of the pipe body due to a breach partway along the pipe body the seawater will directly affect the impedance of the transmission line at that point as the seawater begins to saturate the void or the dielectric material between the electrically conductive members.

Reflections obtained from an electrical test signal introduced into a transmission line can be analysed to determine transmission line faults. Typically a strong reflection is received after a known propagation delay corresponding to the electrical test signal propagating to the opposite end of the transmission line and being reflected back from the unmatched impedance at the opposite end. Other reflections returned from impedance variations along the transmission line from for example, a structural fault, can be analysed. Given knowledge of the electrical propagation speed of a transmission line, the time for the reflection to be returned can be used to determine the location of the impedance variation. Typically the introduced electrical test signal is a very narrow, high energy pulse introduced into one end of the transmission line. The reflected pulse can be observed returning along the transmission line. The time of pulse return indicates the distance down the transmission line where the fault lies (based on the propagation velocity and therefore the time for the signal to travel to the impedance variation and return). The pulse amplitude can be used to give an indication of the seriousness of the fault, and the polarity of the reflection determines whether the fault is tending to an open circuit, or a short circuit. This technique is conventionally referred to as Time Domain Reflectometry (TDR). It will be appreciated that in the case of a pipe body, seawater ingress will cause the transmission line to tend towards a short circuit.

In accordance with the first embodiment of the present invention the signal generator and the receiver are combined to form a transceiver 310 which is coupled by wires 312, 314 to the first and second electrically conductive members 306, 308 within the pipe body 300. The transceiver 310 is coupled to a correlator 316 arranged to correlate a transmitted electrical test signal and a received reflected electrical return signal. The correlator 316 provides a correlation signal which is supplied to a processor 318 for analysis. The transceiver 310, correlator 316 and processor 318 may be referred to as a time domain reflectometer (TDR) 320. It will be appreciated that in alternative embodiments of the present invention the signal generator (or a transmitter) and the receiver may be separate.

The electrical test signal applied between the conductive members 306, 308 by the transceiver 310 is arranged to vary over time. A time varying electrical test signal allows the correlator 316 to generate a correlation signal that indicates the degree of correlation with the electrical return signal at a range of correlation delays which directly correspond to distance along the pipe body (strictly, the correlation delays correspond to twice the distance along the pipe body to a fault giving rise to a signal reflection). Consequently multiple reflections of the electrical test signal, both from far end of the pipe body and impedance variations along the pipe body can be determined. The test signal may be a high frequency pulsed signal. Specifically, the test signal comprises a pulse code modulated signal. In particular embodiments of the invention the electrical test signal comprises a continuous pseudo random coded signal. However, it will be appreciated that the test signal could be discontinuous, for instance a pseudo random burst or chirp signal in which a pseudo random code is transmitted for a short period of time according to a pulse repetition frequency and a duty cycle. Additionally the test signal may not be pseudo random: it could be truly random or it could be a predetermined signal pattern (which may be repeated). Such a test signal may be considered to be a spread spectrum test signal. In the event of repetition of the test signal, it is desirable that the repetition interval is longer than the maximum propagation delay for the test signal to be reflected from the opposite end of the pipe body. The electrical test signal may be generated by the transceiver 310 under the control of the processor 318.

It will be understood that impedance variations within a transmission line formed from electrically conductive members extending along a flexible pipe body may be due to a breach of the outer seawater resistant layer of the pipe body. Seawater ingress into the pipe body is liable to electrically couple the conductive members at the point of the breach, causing a change in the characteristic impedance of the transmission line at the point of the breach, resulting in a signal reflection which may be identified in the correlation signal as a peak or other discernable feature in the correlation signal. The peak may be additional to an expected reflection from the opposite end of the transmission line. It will be appreciated that such a change in the characteristic impedance may also be due to a breach of a barrier layer causing production fluid to enter the pipe body annulus. The processor 318 is arranged to determine the position of a detected impedance variation from the correlation delay of the detected peak, and the magnitude of the changed impedance (indicative of the seriousness of the breach) from the size of the peak. As noted above, other factors may give rise to a change in the impedance, for instance physical damage to the electrically conductive members due to crushing or bending of the pipe body, or significant temperature variation. Such factors may increase the susceptibility of a pipe body to damage, including a breach, and so it is desirable to be able to detect such a change in condition.

It will be appreciated that because a time varying signal, such as a pseudo random code test signal, may be correlated and processed in this way, multiple reflections (and hence multiple changes in condition or defects along the pipe body) can be detected. Furthermore the location of such a defect of change in condition can be determined allowing a visual inspection and, if necessary, maintenance to take place. Advantageously, the first embodiment of the invention allows the condition of a pipe body to be continually monitored either by applying a continuous electrical test signal to the conductive members, or by applying a discontinuous pulsed test signal at regular intervals. Additionally the use of a time varying signal is particularly advantageous compared with the use of a high energy pulse, as used in conventional TDR for coaxial cables, because the peak energy introduced into the pipe body is considerably lower, which is intrinsically safer in a petrochemical environment.

A test signal in accordance with one embodiment of the invention will now be described. The test signal applied to the transmission line comprises of a series of apparently random binary sequences; a pseudo random code (PRC). A PRC is a sequence of binary values which is chosen so that its binary sequence does not repeat throughout the period of the code, and the length of the code is selected to be sufficiently long that for a period of interest there is no repetition. Although each bit sequence is apparently random, the PRC is generated by a computational algorithm using pre-loaded deterministic information. Thus, although within the binary sequence the signal appears to be random, the sequence itself can be repeated at regular intervals. Commonly PRSs are generated using a shift register with appropriate feedback. In one suitable embodiment the PRC is generated in embedded code within a Field Programmable Gate Array (FPGA). The received signal is correlated against the transmitted signal. As the sequences are regularly repeated, the results from sequential autocorrelations can be compared by a microprocessor to examine for changes to the transmission line. A 1024 bit pseudo random binary sequence may be used with a maximum frequency of either 10 MHz or 20 MHz. The binary sequence is aggregated over a minimum of 216 repeats. The resulting signal is presented to the pipeline structure at typically 6 $V_{p-p}$ into a transmission line structure having a typical characteristic impedance of 36 Ω.

It will be understood by the skilled person that careful selection of the properties of the pseudo random electrical test signal can affect the sensitivity of the detection apparatus, while also affecting the power requirements of the apparatus. It will be appreciated that the required resolution for determining the position of a defect in a pipe body (which may be over 1 km in length) could be relatively low. For instance, it may be sufficient to identify the position of a defect to within 5 m allowing visual or manual inspection to identify the precise location. A 50 MHz to 100 MHz pulse rate will provide a detection resolution of the order of 50 cm (depending upon the characteristic impedance of the transmission line before a fault occurs and the propagation speed).

Figure 4:
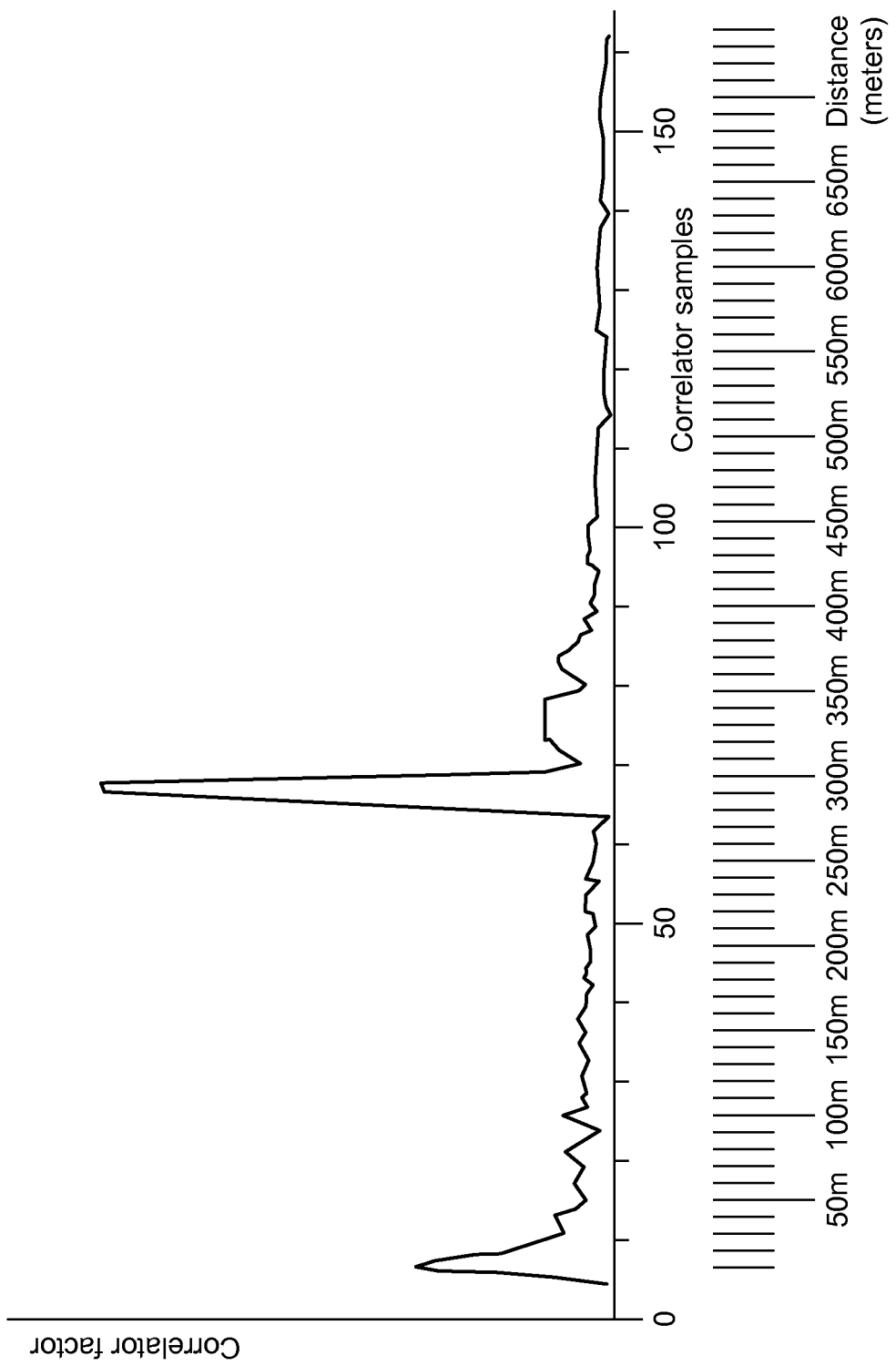
FIG. 4 graphically illustrates the output of a correlator forming part of the detection apparatus of FIG. 3.

The correlation signal output from the correlator 316 is analysed in the processor 318, which alternatively be referred to as a signal analyser. An example of a correlation signal output from the correlator 316 is shown in FIG. 4 which illustrates the correlation signal as a two dimensional array plotting degree of correlation against correlation samples. The correlation samples are representative of time delay between the transmitted electrical test signal and the received electrical return signal. Given knowledge of the propagation velocity, the correlation sample are also representative of distance along the transmission line to the impedance variation giving rise to a reflection (additionally taking into account that the electrical signal must traverse the distance to the anomaly twice). The distance along the transmission line is generally equal to the distance along the pipe body, though this may vary for instance if one or both conductive member comprises a single tensile armour wire which spirals around the pipe body. FIG. 4 plots correlation factor (the correlation magnitude) against correlator samples which is related to distance in metres. It can be seen that there is a significant correlation peak corresponding to an anomaly appearing at around 280 m. The processor 318 may be further arranged to determine whether a correlation peak exceeds a predetermined threshold before providing an output signal indicating that a defect has been detected (and optionally giving location and magnitude of the defect.

In a further embodiment, in place of using structural components of a pipe body to form a transmission line, one or both electrically conductive members may be substituted for a separate electrically conductive tape element. The tape element may take the form for a sensor cable, a conductive wire, or any other suitable elongate electrically conductive structure. Advantageously, this allows the invention to be used in flexible pipes without metallic layers or structural components. Additionally, the tape element may be used in pipe bodies where it is not possible to electrically isolate two electrically conductive structural components. The performance of a separate electrically conductive tape element may be optimised for the specific purposes of the detection system in isolation of the mechanical specification of structural components of a pipe body. The tape element or elements may be placed within a tensile layer of a pipe body, or another suitable layer, with the tape electrically isolated from surrounding structural metal wires. The tape element insulation is preferably permeable to water or other fluids. This can be achieved by using cloth or similar permeable insulation or by placing isolating polymer sections at either side of the tape element so that the interlayer tapes separate the tape element from underlying and overlying layers and the polymer sections from the adjacent structural wires. The insulation is preferably configured and positioned such that in the event of a breach of an outer seawater resistant layer the insulation surrounding the tape element is saturated by seawater. For a non-metallic pipe body no insulation is required so long as the tape elements are spaced apart within the pipe annulus. Advantageously, the use of one or two separate tape elements in the first embodiment of the invention can reduce the necessary modifications to pipe-end fittings to couple the pipe to the detection system.

The lowest preferred industry standard for transmission lines is 50 ohms, and the detection apparatus in accordance with embodiments of the present invention is designed around this so as to allow the use of standard lead in cables and connectors to couple to the electrically conductive elements extending along the pipe to form the transmission line. However, a pipe structure typically has a characteristic impedance around 35Ω or less. Therefore to match the detection apparatus to the pipe requires an impedance matching transformer in the pipe end fitting. Advantageously, the use of separate tape elements, such as sensor cables or wires, extending along the pipe to form the transmission line, in place of the use of structural elements of the pipe, allows greater control over the characteristic impedance of the transmission line. In certain embodiments the careful selection of tape elements allows the pipe transmission line to have a characteristic impedance which is compatible with the detection apparatus, for instance 50Ω, removing the need for a transformer.

As a further alternative, in place of a separate electrically conductive tape element, one or more tensile armour wires or layers may be electroplated, for instance with a copper coating, to lower the resistance of the armour wire. The transmission line properties of the tensile armour wires may thus be closely controlled without impacting upon the structural properties of the armour wires. Additionally insulation within the transmission line may be formed from a material that is permeable to fluids, but arranged to selectively block certain fluids, for instance $H_2S$ which may be desirable in certain embodiments.

It will be appreciated that in the event of a breach of an outer seawater resistant layer the pipe body annulus will begin to fill with water. The consequence of this is that, while the impedance of the whole transmission line will be affected, there will no longer be a sharp variation in impedance at the point of the original breach. Consequently, certain embodiments of the present invention may preferably continuously monitor a pipe body for an indication of a possible defect and record observed signal reflections, including recording the magnitude of a reflection and its location, such that this indication of a defect is not lost as the surrounding portions of the transmission line assume the same, reduced impedance.

Figure 8:
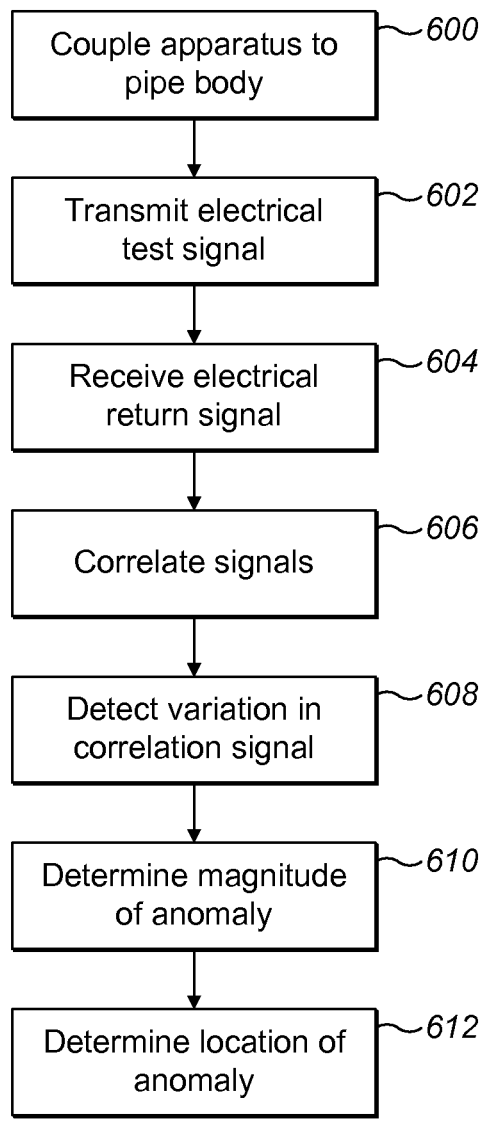
FIG. 8 is a flow chart illustrating a detection method in accordance with the first embodiment of the invention.

Referring now to the flow chart of FIG. 8, a detection method in accordance with the first embodiment of the present invention will now be described. At step 600 the detection apparatus illustrated in FIG. 3 is coupled to an electrically conductive member within the pipe body and to a sea water electrode. At step 602 an electrical test signal as described above is coupled between the electrically conductive members. At step 604 an electrical return signal is received. At step 606 the test signal and the return signal are correlated to provide a correlation signal. At 608 the correlation signal is processed to detect variations which may be indicative of a pipe body defect or other change of condition. At 610 the magnitude of a variation, in particular the magnitude of a newly appearing peak in the correlation signal, is determined to provide an indication of the severity of a defect or a change in pipe body condition. At 612 the location of a detected anomaly may be determined. It will be appreciated that in practice the method of FIG. 8 is not a linear process and in certain embodiments the test signal may be continuously or substantially continuously applied to the electrically conductive members. Consequently a return signal may be continuously received and the correlation signal may be continuously generated and processed.

Figure 5:
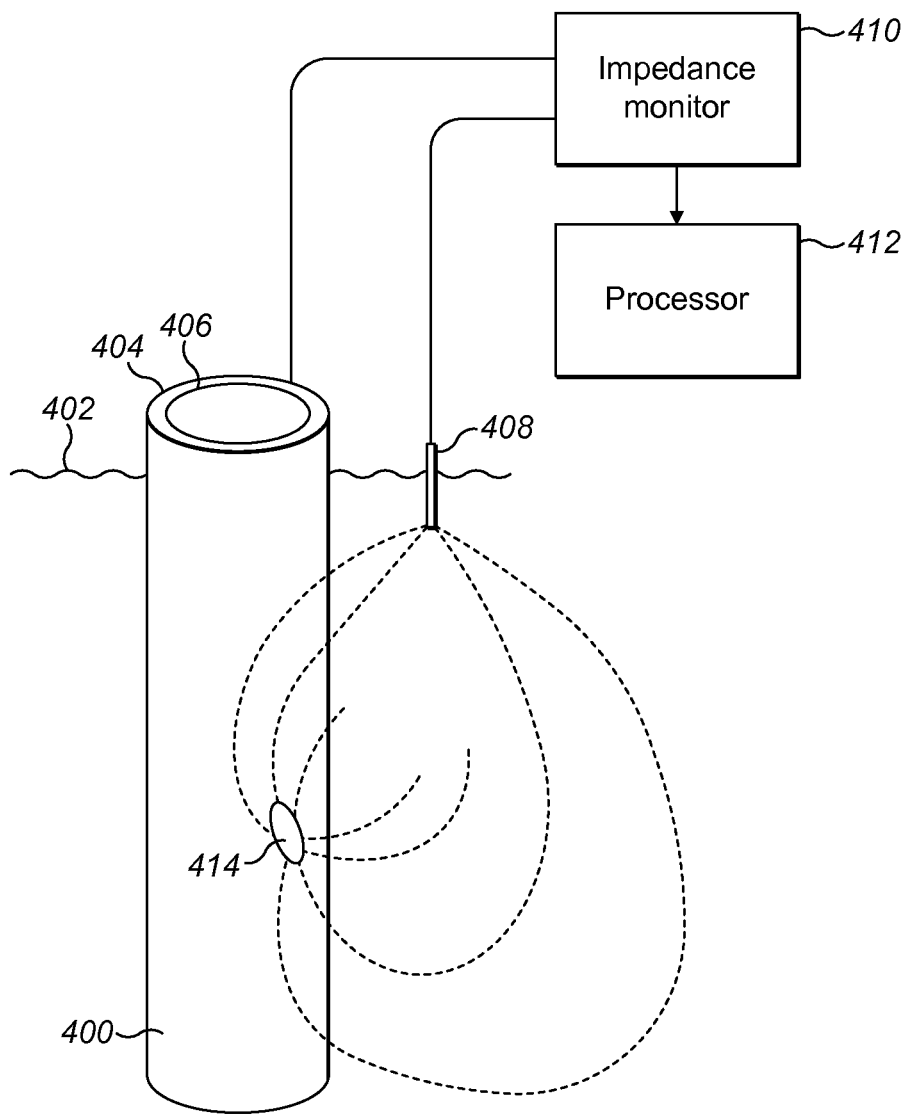
FIG. 5 illustrates a detection apparatus in accordance with a second embodiment of the invention.

FIG. 5 illustrates a detection apparatus in accordance with a second embodiment of the present invention. As for the first embodiment of the invention, the detection apparatus is arranged to detect a change to a flexible pipe body which may be indicative either of a defect (and in particular a breach which allows seawater or other fluids into the pipe body annulus). The detection apparatus may be coupled to a warning system arranged to provide an output signal to an operator of the flexible pipe alerting the operator to potential damage to the pipe. The output signal may, for instance, be a visual or audible alarm.

Certain aspects of the second embodiment of the present invention are similar or identical to aspects of the first embodiment of the present invention and so their description will not be repeated. In particular, the construction of a flexible pipe body which may be coupled to the detection apparatus may be the same. As will be described below, the detection apparatus illustrated in FIG. 5 need couple only to a single electrically conductive member extending at least partially along the length of a pipe body. The electrically conductive member may comprise a metallic structural component such as a single tensile armour wire or a tensile armour wire layers, or a separate tape element as described above.

The outer seawater resistant layer of a flexible pipe body may be manufactured from a polymer material with known intrinsic electrical insulation properties. Sea water has known electrical conduction properties, though this may vary from location to location, for instance due to variation in the salinity of the seawater, and so the second embodiment of the invention may require calibration before use to adapt to local conditions. A physical breach in the form of an aperture in the outer seawater resistant layer of a flexible pipe permits a conductive path between the sea water and the steel internal structure of the pipe body. In accordance with the second embodiment of the present invention an electrical impedance measurement made between seawater surrounding a flexible pipe and the internal metallic structure of the pipe body provides a means of indicating the presence of a breach. Specifically, in the event that the measured impedance drops, it can be inferred that a breach has occurred and seawater is in contact with the internal metallic structure of the pipe body.

Referring to FIG. 5, this shows a flexible pipe body 400, which as discussed above may comprise a riser. The pipe body is at least partially surrounded by seawater, schematically illustrated by the pipe body extending below the surface level 402 of the sea. As discussed above, such a flexible pipe body is constructed from multiple layers of polymer barrier, including an outer seawater resistant layer 404 and at least one layer of metallic structural elements 406, for instance the tensile armour layers 105, 106 of FIG. 1. A seawater electrode 408 is in contact with seawater in proximity to the pipe body 400. An impedance monitor 410 is coupled to the seawater electrode 408 and either a metallic structural component 406 of the pipe body 400 or a separate tape element within the pipe body. The impedance monitor 410 provides a measurement of the impedance between the seawater electrode 408 and the pipe body 400. The impedance measurement is supplied to a processor 412 which is arranged to detect an impedance drop, for instance from approximately 1 MΩ (approximately equal to a impedance of a polymer barrier layer) to approximately 5Ω (the approximate impedance of seawater). In one embodiment the impedance monitor 412 is arranged to measure impedance in the range of 0-10 kΩ. An impedance above 10 kΩ is registered as the maximum 10 kΩ due to the measurement system saturating at that value. Advantageously, this accurately records the absence of a polymer barrier layer while allowing greater measurement resolution at lower impedance values. If there is any seawater conductivity path between the structure of the pipe body and the seawater electrode the measured impedance is well below 10 kΩ The processor 412 is further arranged to determine whether this impedance drop is indicative of a breach of the outer seawater resistance layer of the pipe body, for instance by determining whether the magnitude of the impedance drop exceeds a predetermined threshold. The processor 412 is arranged to provide an appropriate output signal as described above in connection with processor 318 of FIG. 3.

Unlike the predominantly electron flow conduction in metals, the electrical conduction in seawater is dependent on ion mobility, and this leads to significant variation in observed conductivity with the frequency of the applied measurement excitation. This is shown schematically in the FIG. 6 which shows relative attenuation of an applied alternating current signal at various low frequencies and between electrodes spaced at 10 m, 100 m, and 1 Km. The second embodiment of the present invention takes advantage of the attenuation data of FIG. 6 by applying frequency agile excitation of the impedance monitor 410, comparing the results obtained at various frequencies, and from that information determining an approximate location of the breach. In certain embodiments the excitation frequency of the impedance monitor is in the range 10 Hz to 1 kHz. In other embodiments the maximum excitation frequency of the impedance monitor may be 100 kHz. It will be appreciated by the skilled person that the detection system of FIG. 5 could also operate using DC test signals to determine whether there is a pipe defect through detected seawater conduction to the seawater electrode. However, it will be understood that this would not allow the detection of location of the defect. Furthermore there would be additional complications to be overcome due to electro-chemical offsets, polarisation and interference with the pipe cathodic protection system (discussed below).

Figure 7:
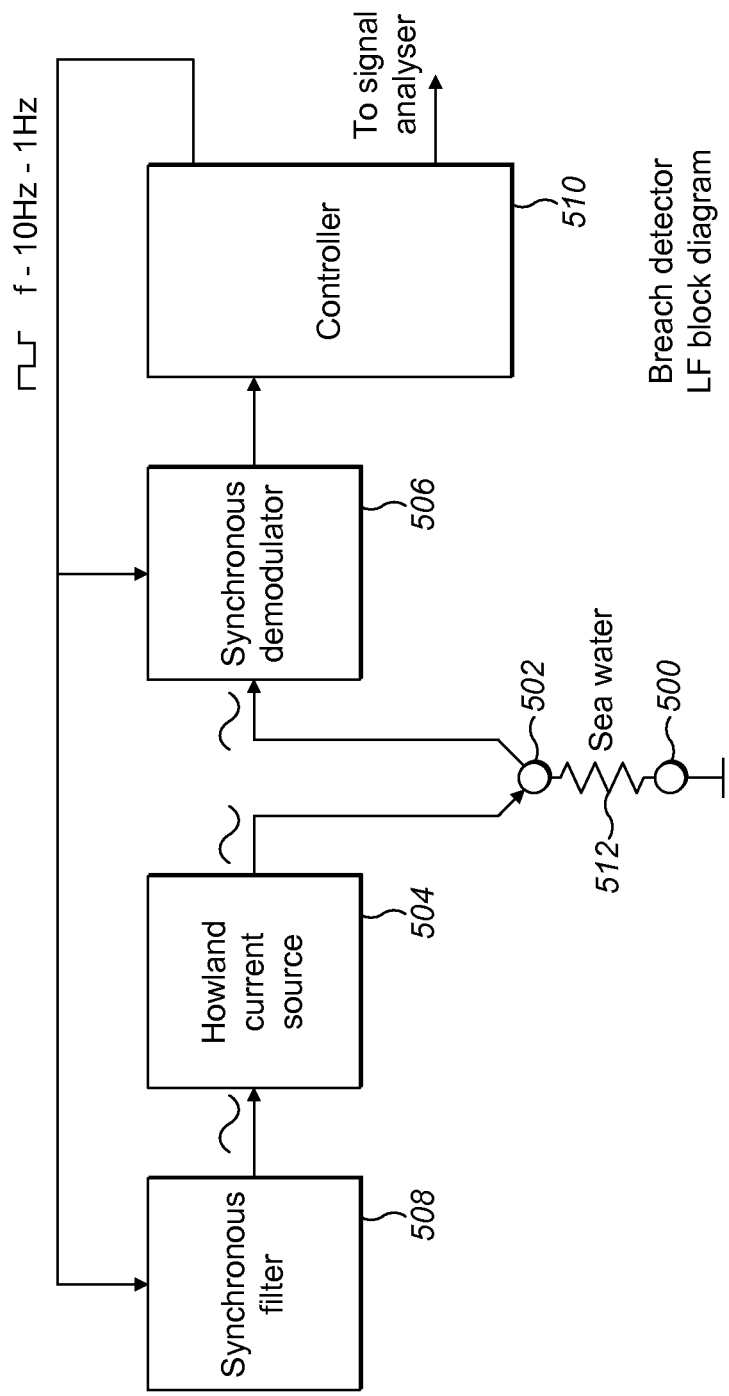
FIG. 7 illustrates an impedance monitor forming part of the detection apparatus of FIG. 5.

The impedance monitor is shown in greater detail in FIG. 7. A first electrode 500 is coupled to Earth and a second electrode 502 is coupled between a Howland current source 504 and a synchronous demodulator 506. It will be appreciated that the first electrode may be the seawater electrode 408 and the second electrode may be within the pipe body. Specifically, the seawater electrode may be the metalwork (i.e. "Earth") of the supporting vessel or rig. The impedance monitor may operate in either a voltage or current source mode. In FIG. 7 a Howland current source 504 is used as it provides greater linearity of response. The Howland current source 504 is shown connected to the second electrode. The Howland current source 504 supplies a current to the pipe body in response to an input signal supplied by a synchronous filter 508. The current may be AC current. In one embodiment, preferably the signal may be a sinusoidal waveform AC current. Other waveforms, for instance a square wave could be used, however sinusoidal is preferred because then there are no harmonics present, which could interfere with the operation of the frequency dependent range measurement system. That is, the applied electrical test signal may be AC. In other embodiments a voltage source may be used. The synchronous filter 508 provides a signal under the control of a pulsed control signal from controller 510, which additionally supplies the same control signal to the synchronous demodulator 506. The synchronous demodulator 506 is arranged to analyse the voltage generated across the insulating boundary of the pipe body and the seawater at each frequency. The synchronous demodulator 506 supplies an output signal to the controller 510, which is indicative of the voltage of the second electrode 502 relative to Earth. In the event of a breach of the polymer barrier, the voltage of the second electrode 502 is dependent upon the applied current and the seawater impedance between the electrodes 500, 502 indicated by resistor symbol 512. The controller 510 is arranged to generate an output signal indicative of the impedance between the electrodes 500, 502 by comparison of the supplied current and the measured voltage. The output signal is provided to the processor 412, which is arranged to determine whether a breach is detected.

Figure 6:
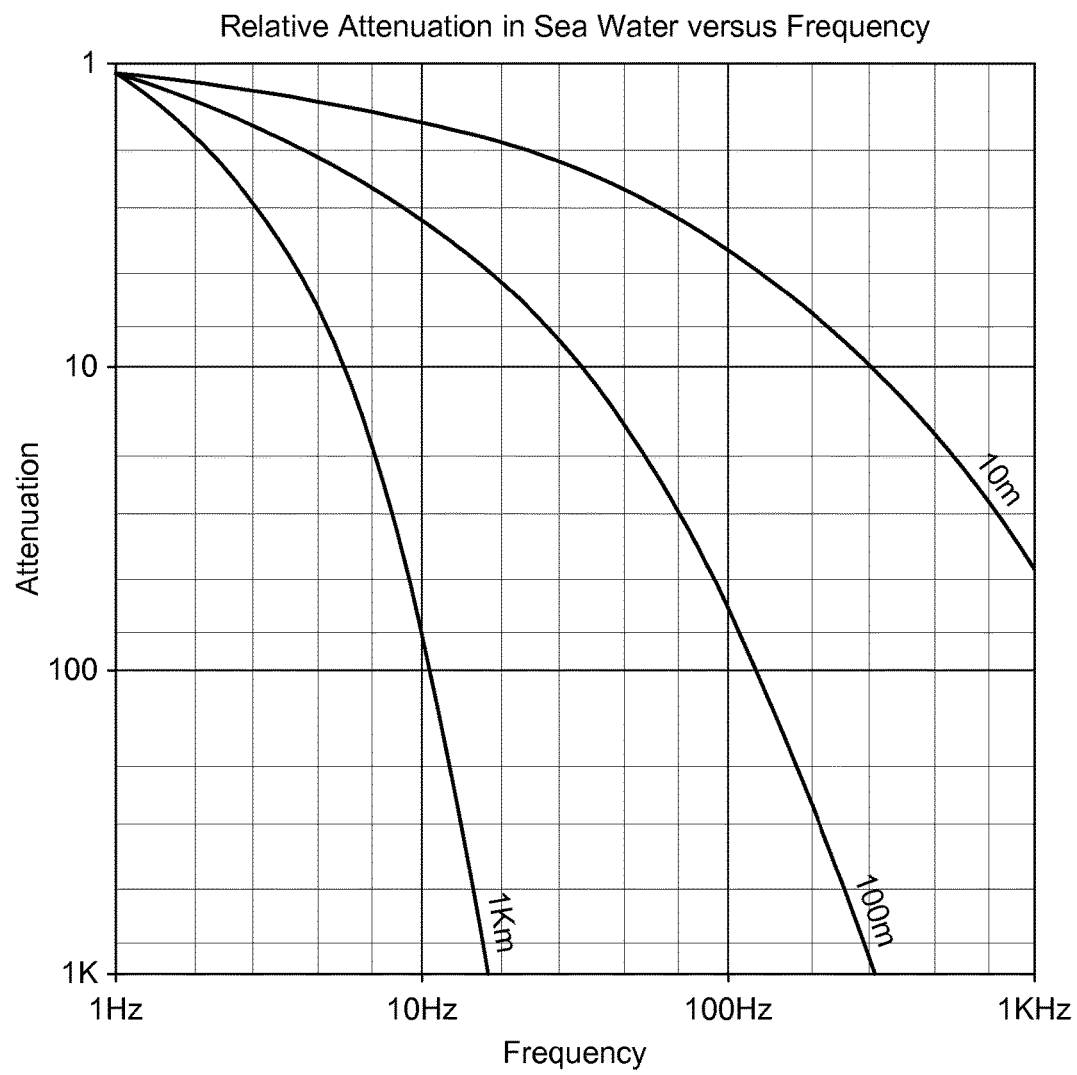
FIG. 6 is a graph illustrating the attenuation of an electrical signal relative to the frequency of the signal for three different distances.

In the event that a breach (schematically shown at 414 in FIG. 5) is detected through a step change in the impedance the processor 412 is arranged to instruct the impedance monitor to perform impedance measurements at a range of excitation frequencies (for instance 10 Hz, 30 Hz, 100 Hz, 300 Hz and 1 kHz), which by cross reference to the graph of FIG. 6 (or by reference to a look up table within the processor 412) allow an estimation of the position of the breach to be determined. The accuracy of this computation is dependent on a number of factors including the size of the breach, the salinity and temperature of the sea water, the attitude of the pipe body (e.g. vertical to horizontal) and the electrical conductivity of the steel inner structure.

Figure 9:
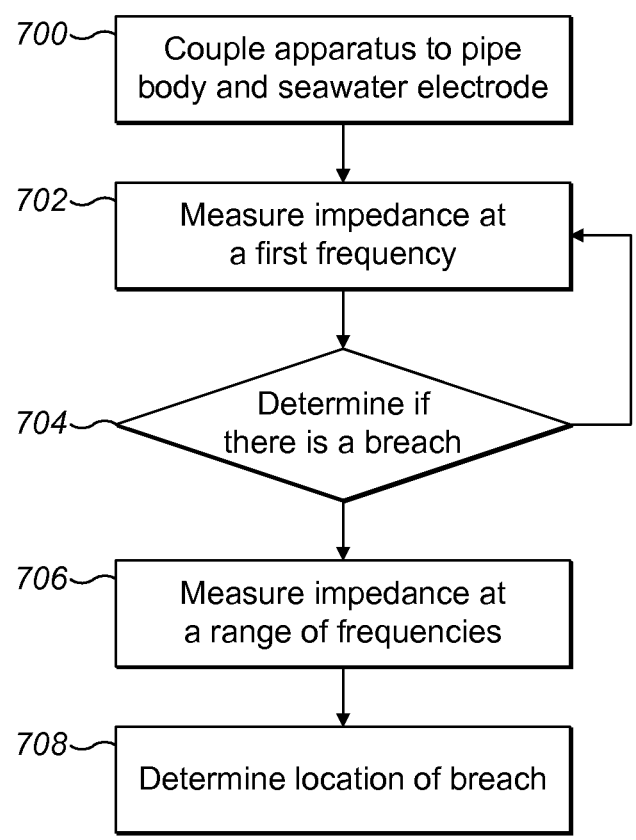
FIG. 9 is a flow chart illustrating a detection method in accordance with the second embodiment of the invention.

Referring now to the flow chart of FIG. 9, a detection method in accordance with the second embodiment of the present invention will now be described. At step 700 the detection apparatus illustrated in FIG. 3 is coupled to an electrically conductive member within the pipe body and to a sea water electrode. At step 702 the impedance between the electrodes is measured at a first frequency. At step 704 a determination is made whether a breach has been detected by the magnitude of any detected drop in impedance. At step 706 if a breach is detected the impedance is measured at a range of frequencies. At step 708 the frequency and impedance data is used to determine the location of a breach. If on the other hand at step 704 it is determined that no breach has been detected, the process returns to step 702.

Advantageously, embodiments of the present invention described above do not interfere with active cathodic protection systems coupled to pipe bodies if AC current is used. The AC signals, when applied to the electrically conductive members or separate tape elements within the pipe body have no effect upon a DC cathodic protection system.

With the above-described arrangement defects including breaches of an outer seawater resistant layer of a pipe body, and other variations of the condition of a flexible pipe body can be detected in a timely manner, allowing further inspection, and if necessary maintenance, to take place.

It will be clear to a person skilled in the art that features described in relation to any of the embodiments described above can be applicable interchangeably between the different embodiments. The embodiments described above are examples to illustrate various features of the invention. It will be further apparent that the detection apparatuses and methods described in connection with FIG. 3 and FIG. 5 may be used in combination. For instance the detection apparatus of FIG. 5 may be used to detect a breach in an outer seawater resistant barrier layer before implementing the detection apparatus of FIG. 3 to determine the location of the breach (thereby minimising the use of the more data intensive system of FIG. 3). Alternatively, the detection apparatus of FIG. 3 may be used to detect a breach in an outer seawater resistant barrier layer before implementing the detection apparatus of FIG. 5 to determine the location of the breach. As a further alternative, both apparatus may be used simultaneously, or alternately, in order to provide redundancy, in the event of failure of either apparatus, and greater confidence that a seawater breach has been correctly detected and located. In the event that both detection apparatuses are applied to a single flexible pipe, the electrically conductive members may be separate for each apparatus or they may overlap.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:
1. A pipeline apparatus comprising:
a pipe body including annular innermost and outermost fluid impermeable barrier layers;
first and second electrically conductive members extending at least partially along the length of the pipe body between the innermost and outermost barrier layers and electrically isolated from one another to form an electrical transmission line;

an end fitting coupled to at least one end of the pipe body; and a detection apparatus coupled to the end fitting;

wherein the detection apparatus comprises:

a signal generator coupled to the first and second electrically conductive members, the signal generator being arranged to generate an electrical test signal and to apply the test signal between the first and second electrically conductive members, the test signal comprising a pulse code modulated electrical signal;

a receiver coupled to the first and second electrically conductive members and arranged to receive an electrical return signal comprising a reflection of the test signal;

a correlator arranged to correlate the test signal with the return signal and to determine a correlation signal; and a processor arranged to detect variation of the correlation signal, and to determine if a detected variation is indicative of a pipe defect;

wherein at least one of the electrically conductive members comprises an electrically conductive tape element; and wherein the signal generator and the receiver are coupled to a first end of the electrically conductive members, said pipeline apparatus further comprising a second detection apparatus, the second detection apparatus comprising:

an impedance monitor coupled to and arranged to measure the impedance between an electrically conductive member extending at least partially along the length of the pipe body and a seawater electrode in contact with seawater surrounding at least part of the pipe body in response to an electrical test signal applied to the electrically conductive member at first and second frequencies; and a processor arranged to detect variation of the measured impedance for an electrical test signal at a first frequency, and if a variation of the measured impedance is detected, to determine if the variation is indicative of a pipe defect, and if so to determine the distance from the seawater electrode to a pipe defect by comparison of the measured impedances at the first and second frequencies.

2. A pipeline apparatus comprising:

a pipe body including:

a tubular inner sheath extending along a length of the pipe body and defining a fluid impermeable barrier layer;

a tubular outer sheath extending along the length of the pipe body and defining a fluid impermeable barrier layer, the tubular inner sheath and the tubular outer sheath defining therebetween a pipe body annulus extending along the length of the pipe body; and an electrically conductive member extending at least partially along the length of the pipe body within the pipe body annulus;

an end fitting coupled to said tubular inner sheath and said tubular outer sheath;

a seawater electrode disposed separate from and outside of the pipe body and in contact with seawater surrounding at least a part of the flexible pipe; and a detection apparatus coupled to the end fitting, wherein the detection apparatus comprises:

an impedance monitor coupled to the electrically conductive member and the seawater electrode, the impedance monitor being arranged to measure an impedance between the electrically conductive member and the seawater electrode through seawater surrounding at least part of the pipe body in response to an electrical test signal applied to the electrically conductive member at a first frequency and a second frequency; and a processor arranged to detect a variation in the impedance measured in response to the electrical test signal at the first frequency, and in an event a variation in the impedance is detected, determine whether the variation is indicative of a breach of the tubular outer sheath causing seawater to enter the pipe body annulus, and if so, determine a distance from the seawater electrode to the breach by comparing the impedance measured at the first frequency with the impedance measured at the second frequency.

3. The pipeline apparatus according to claim 2, wherein the electrically conductive member comprises a metallic structural member of the pipe body.

4. The pipeline apparatus according to claim 2, wherein the electrically conductive member comprises an electrically conductive tape element.

5. The pipeline apparatus according to claim 2, further comprising a second detection apparatus, the second detection apparatus comprising:

a signal generator coupled to a pair of electrically conductive members extending at least partially along the length of the pipe body and electrically isolated from one another to form an electrical transmission line, the signal generator being arranged to generate an electrical test signal and to apply the test signal between the pair of electrically conductive members, the test signal comprising a pulse code modulated electrical signal;

a receiver coupled to the pair of electrically conductive members and arranged to receive an electrical return signal comprising a reflection of the test signal;

a correlator arranged to correlate the test signal with the return signal and to determine a correlation signal; and a processor arranged to detect a variation in the correlation signal and in an event the variation in the correlation signal is detected, determine whether the detected variation is indicative of a breach of the tubular inner sheath or the breach of the tubular outer sheath causing fluid to enter the pipe body annulus;

wherein at least one of the electrically conductive members comprises an electrically conductive tape element; and wherein the signal generator and the receiver are coupled to a first end of the electrically conductive members.

6. The pipeline apparatus according to claim 5, wherein at least one of the electrically conductive members comprise a first metallic structural member of the pipe body.

7. A method of forming a pipeline apparatus, the method comprising:

providing a pipe body including:

a tubular inner sheath extending along a length of the pipe body defining a fluid impermeable barrier layer;

a tubular outer sheath extending along the length of the pipe body defining a fluid impermeable barrier layer, the tubular inner sheath and the tubular outer sheath defining therebetween a pipe body annulus extending along the length of the pipe body; and an electrically conductive member extending at least partially along the length of the pipe body within the pipe body annulus;

providing a seawater electrode, the electrode being disposed separate from and outside of the pipe body and in contact with seawater surrounding at least part of the flexible pipe; and coupling an end fitting to said tubular inner sheath and said tubular outer sheath;

coupling a detection apparatus to the end fitting, wherein the detection apparatus comprises:

an impedance monitor arranged to measure an impedance between the electrically conductive member and the seawater electrode through seawater surrounding at least part of the pipe body in response to an electrical test signal applied to the electrically conductive member at a first frequency and a second frequency; and a processor arranged to detect a presence of variation in the impedance measured in response to the electrical test signal at the first frequency, and in an event the presence of variation in the impedance is detected, determine whether the variation is indicative of a breach of the tubular outer sheath causing seawater to enter the pipe body annulus, and if so determine a distance from the seawater electrode to the breach by comparing the impedance measured at the first frequency with the impedance measured at the second frequency; and coupling the impedance monitor to the electrically conductive member and the seawater electrode.

8. The pipeline apparatus according to claim 2, wherein the impedance monitor is arranged to apply electrical test signals to the electrically conductive member at a plurality of frequencies between 10 Hz and 100 kHz.

9. The pipeline apparatus according to claim 2, wherein the impedance monitor comprises a current source arranged to supply an electrical test signal to the electrically conductive member, and a voltage meter arranged to determine the generated voltage at the electrically conductive member relative to the seawater electrode.

10. The pipeline apparatus according to claim 2, wherein the voltage meter is a synchronous demodulator and the impedance monitor further comprises a controller arranged to provide a frequency control signal to the current source and the synchronous demodulator.

11. A method of detecting defects within a flexible pipe at least partially surrounded by seawater, the method comprising:

coupling an impedance monitor between an electrically conductive member extending at least partially along a length of a flexible pipe body within a pipe body annulus extending along the length of the pipe body and a seawater electrode disposed separate from and outside of the pipe body and in contact with seawater surrounding at least part of the flexible pipe;

generating an electrical test signal at the impedance monitor and applying the test signal to the electrically conductive member at a first frequency and a second frequency;

measuring an impedance between the electrically conductive member and the seawater electrode through seawater surrounding at least part of the pipe body;

detecting a variation in the measured impedance for an electrical test signal at a first frequency; and determining if the variation in the measured impedance is indicative of a breach of the tubular outer sheath causing seawater to enter the pipe body annulus, and if so determining a distance from the seawater electrode to the breach by comparing the measured impedances at the first and second frequencies;

wherein the pipe body annulus is defined between a tubular internal sheath extending along the length of the pipe body defining a fluid impermeable barrier layer and a tubular outer sheath extending along the length of the pipe body defining a fluid impermeable barrier layer.

* * * * *